United States Patent
Hirshenbein et al.

(10) Patent No.: US 7,657,000 B2
(45) Date of Patent: Feb. 2, 2010

(54) METHOD AND APPARATUS FOR DUAL ENERGY RADIOGRAPHY

(75) Inventors: Aviv Hirshenbein, Tel-Aviv (IL); Ehud Dafni, Caesarea (IL); Ilan Sivan, Yokneam (IL)

(73) Assignee: CMT Medical Technologies Ltd., Yokneam Ilit (IL)

( * ) Notice: Subject to any disclaimer, the term of this patent is extended or adjusted under 35 U.S.C. 154(b) by 89 days.

(21) Appl. No.: 11/936,999

(22) Filed: Nov. 8, 2007

(65) Prior Publication Data

US 2008/0123802 A1 May 29, 2008

Related U.S. Application Data

(60) Provisional application No. 60/860,901, filed on Nov. 27, 2006.

(51) Int. Cl.
*H05G 1/64* (2006.01)
*G01N 23/087* (2006.01)

(52) U.S. Cl. .................. 378/98.11; 378/98.9
(58) Field of Classification Search ............ 378/62, 378/98.8, 98.9, 98.11, 98.12
See application file for complete search history.

(56) References Cited

U.S. PATENT DOCUMENTS

| | | | | |
|---|---|---|---|---|
| 4,855,598 A | * | 8/1989 | Ohgoda et al. | 250/582 |
| 5,187,731 A | * | 2/1993 | Shimura | 378/207 |
| 5,237,176 A | * | 8/1993 | Ito | 250/587 |
| 5,931,780 A | * | 8/1999 | Giger et al. | 600/407 |
| 6,240,201 B1 | * | 5/2001 | Xu et al. | 382/130 |
| 6,273,606 B1 | * | 8/2001 | Dewaele et al. | 378/174 |
| 6,421,419 B1 | * | 7/2002 | Sakaida | 378/98.11 |
| 7,248,726 B2 | * | 7/2007 | Sasada | 382/132 |
| 2007/0153973 A1 | * | 7/2007 | Huo et al. | 378/54 |
| 2008/0011960 A1 | * | 1/2008 | Yorkston et al. | 250/370.09 |

* cited by examiner

*Primary Examiner*—Allen C. Ho
(74) *Attorney, Agent, or Firm*—William H. Dippert; Eckert Seamans Cherin & Mellott, LLC

(57) ABSTRACT

There is provided an apparatus and method for x-ray imaging of a subject that comprises an x ray source emitting a spectrum of radiation of low energy component as well as high energy component to be attenuated by the subject. At least one CR plate adapted to absorb mainly the radiation of low energy component that was attenuated by the subject is provided, wherein low energy x rays image can be attained on the CR plate as well as a DR plate that is adapted to absorb the high energy component, wherein the DR plate is placed further to the CR plate relative to the subject so as to attain image from higher energy x rays. The apparatus is further provided with a processor adapted to process the CR and DR images obtained in a single irradiation of the subject so as to obtain a third combined processed image.

22 Claims, 4 Drawing Sheets

METHOD AND APPARATUS FOR DUAL ENERGY RADIOGRAPHY

This present invention claims the benefit of earlier U.S. provisional patent application Ser. No. 60/860,901 filed on 27 of Nov. 2006 by Hirshenbein et al. and entitled "Method and Apparatus for Dual Energy Radiography".

FIELD OF THE INVENTION

The present invention relates to digital radiography. More particularly, the present invention relates to dual energy digital radiography.

BACKGROUND OF THE INVENTION

Digital Radiographic imaging is used to generate digital projection X-ray images of subjects, typically human patients. Common technologies in the art are Computed Radiography (CR) and Digital Radiography (DR). CR uses stimulable phosphor sheets that capture and absorb the X ray energy, store it and then the phosphor sheets are being scanned to provide the digital image. In DR, the radiation strikes a plate onto which large area position sensitive detectors are generating a digital image in real time.

The imaged subjects have internal structures that differ in X ray absorption due to different thickness, density and atomic composition. The internal structures may have different response to different X ray energy range, thus allowing to enhance the contrast between certain structures by different choice of beam energy. In dual energy scanning techniques, two images are obtained at two different beam energy ranges and a third improved image is usually generated by normalization and/or another mathematical manipulation such as subtraction technique, as an example. This technique had been used for the last two decades. The improvement may be directed to elimination of certain structures (e.g. bones in soft tissue imaging), differentiating between structures (e.g. bone from contrast agent, explosive from other materials) or enhancing the contrast between neighboring structures (e.g. tissues in a patient).

The existing methods such as multislice CT are relatively excessive radiation-prone and there is a need to reduce the amount of radiation that is used during patient imaging. In dual energy subtraction, acquisition of two images offers less radiation.

The ability to convert computed radiography combined with digital radiography, each having its unique features to dual energy system while maintaining relatively low doses of radiation opens the opportunity to many potential medical applications.

SUMMARY OF THE INVENTION

It is an object of the present invention to provide low cost solution for converting conventional digital radiography system to dual energy system.

It is another object of the present invention to provide a digital radiography system that can produce high-quality images while utilizing relatively lower doses of radiation.

It is therefore provided in accordance with a preferred embodiment of the present invention, an apparatus for x-ray imaging of a subject, comprising:

an x ray source emitting a spectrum of radiation of low energy component as well as high energy component to be attenuated by the subject;

at least one CR plate adapted to absorb mainly said radiation of low energy component that was attenuated by the subject, wherein low energy x rays image can be attained on said at least one CR plate;

a DR plate adapted to absorb said high energy component, wherein said DR plate is placed further to said CR plate relative to the subject, so as to attain image from higher energy x rays;

a processor adapted to process the CR and DR images obtained in a single irradiation of the subject so as to obtain a third combined processed image.

Furthermore, in accordance with another preferred embodiment of the present invention, said at least one CR plate is a stimulable phosphor sheet.

Furthermore, in accordance with another preferred embodiment of the present invention, said DR plate is FPD.

Furthermore, in accordance with another preferred embodiment of the present invention, said at least one CR plate is configured to acquire image from a portion of the subject and wherein said DR plate is placed to acquire image from another portion of the subject.

Furthermore, in accordance with another preferred embodiment of the present invention, an absorbing plate is further placed adjacent to said at least one CR plate or said DR plate.

Furthermore, in accordance with another preferred embodiment of the present invention, said absorbing plate is placed between said at least one CR plate and said DR plate.

Furthermore, in accordance with another preferred embodiment of the present invention, an anti-scatter grid is further placed adjacent to said at least one CR plate or said DR plate.

Furthermore, in accordance with another preferred embodiment of the present invention, said anti-scatter grid is placed between said at least one CR plate and said DR plate.

Furthermore, in accordance with another preferred embodiment of the present invention, an AEC detector is placed between said at least one CR plate and said DR plate.

Furthermore, in accordance with another preferred embodiment of the present invention, an AEC detector is placed between said at least one CR plate and the subject.

Furthermore, in accordance with another preferred embodiment of the present invention, said DR plate is placed within a bucky that is provided with rails adapted to receive at least one of said at least one CR plate.

Furthermore, in accordance with another preferred embodiment of the present invention, said DR plate is a scintillator-amorphous silicon type.

It is provided in accordance with yet another preferred embodiment of the present invention, method of x-ray imaging of a subject comprising:

exposing the subject to X radiation;

placing at least one CR plate adapted to absorb said radiation that was attenuated by the subject, said at least one CR plate is optimized to absorb preferably a low energy component of said radiation;

placing further downstream a DR detector for detecting radiation that was attenuated by the subject and the CR, wherein said detector is optimized to absorb the high energy components of the radiation;

scanning the CR to obtain a first digital image;

processing said first digital image to match exactly the DR image;

obtaining a third combined image by processing said first digital image and said DR image.

Furthermore, in accordance with another preferred embodiment of the present invention, said processing said first digital image comprises registering, zooming, and aligning.

Furthermore, in accordance with another preferred embodiment of the present invention, the method further comprises placing an absorbing plate adjacent said at least one CR plate.

Furthermore, in accordance with another preferred embodiment of the present invention, the method further comprises placing an anti-scatter grid adjacent said at least one CR plate.

Furthermore, in accordance with another preferred embodiment of the present invention, the method further comprises placing AEC adjacent said at least one CR plate.

Furthermore, in accordance with another preferred embodiment of the present invention, obtaining a third combined image is performed by linear algebra operations such as multiply each by a constant, add/subtract, or multiply each by a parameter that is in itself a function of the pixel value or a value of the pixel and its neighboring pixels.

Furthermore, in accordance with another preferred embodiment of the present invention, obtaining a third combined image is performed by treating said first digital image as an "indicator" image, where coordinates of certain pixels are used to manipulate the DR image, which is used as a target image, while all the other pixels are left untouched or are handled differently.

Furthermore, in accordance with another preferred embodiment of the present invention, obtaining a third combined image is performed by choosing an ROI on one of said first digital image or said DR image and perform an analysis only in said ROI.

Furthermore, in accordance with another preferred embodiment of the present invention, said method further comprising calculating BMD values said first digital image and said DR image.

Additionally and in accordance with yet another preferred embodiment of the present invention, said method further comprises finding calcified nodules in bone imaged on said third combined image.

BRIEF DESCRIPTION OF THE FIGURES

In order to better understand the present invention and appreciate its practical applications, the following Figures are attached and referenced herein. Like components are denoted by like reference numerals.

It should be noted that the figures are given as examples and preferred embodiments only and in no way limit the scope of the present invention as defined in the appending Description and Claims.

DETAILED DESCRIPTION OF THE INVENTION AND THE FIGURES

The present invention provides new and unique apparatii designs adapted for converting conventional digital radiography system and computed radiology system to dual energy system. As mentioned herein before, dual energy subtraction is a method in which "low energy image" and "high energy image" of a patient are captured during a single examination. The practical result of this is the construction of a pair of energy subtraction images. There are configurations that are already used in the art; one example is two stacked detectors separated by a copper filter that differentially record the fluency of x-ray photons transmitted through the patient using a single x-ray exposure. Another configuration involves dual x-ray exposure of a patient to x-ray beams with two distinct spectra, temporally separated by an interval of time, using a single detector.

Under either of the configurations, the two captured images are mathematically combined through a weighted subtraction as an example to provide powerful information to diagnostics.

According to one aspect of the present invention, a diagnostically powerful combination takes advantage of the inherent sensitivity of CR plates to low energies and DR plates to all energies. The two types of detectors are being stacked in order to receive overall information through a single exposure to x-ray beam.

According to other aspects of the present invention, other features such as automatic exposure control (AEC) sensor(s), absorbers, multiple CR plates etc. are added to the "sandwiched" detectors in order to increase its sensitivity.

Figure 1:
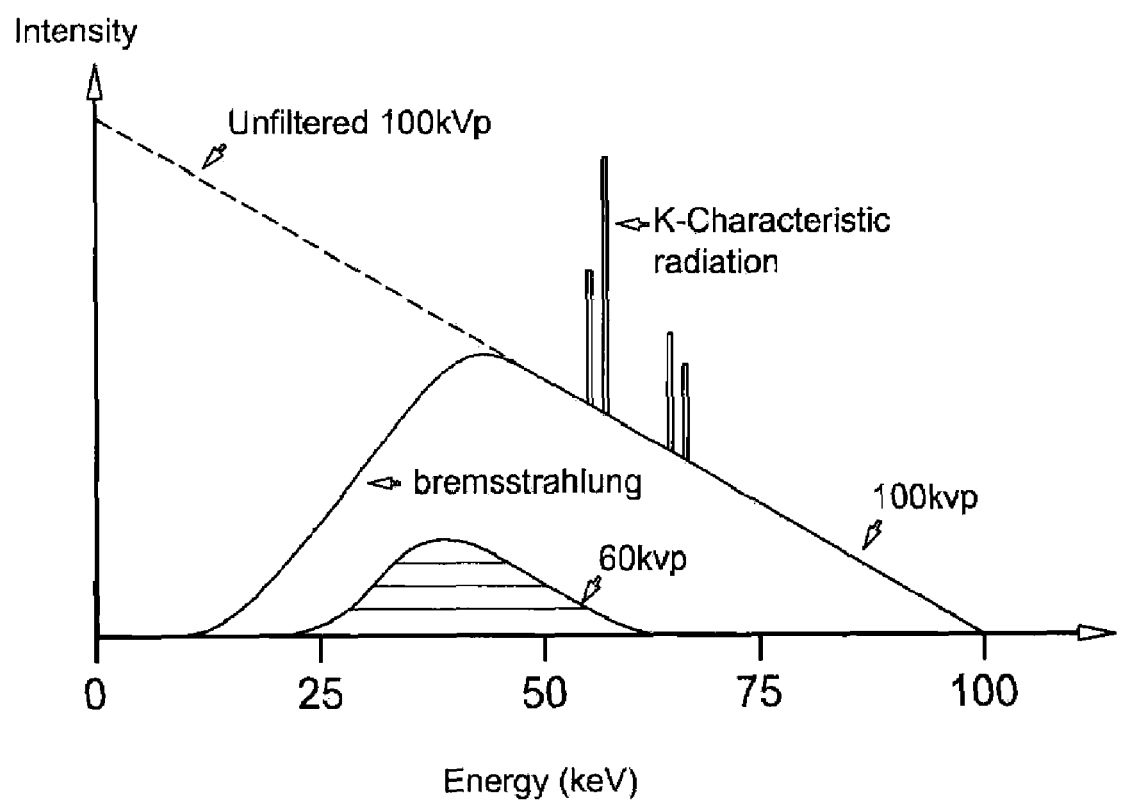
FIG. 1 illustrates a typical X-ray spectrum.

Generally, the present invention is designed to generate dual energy images by a combination of CR plate mounted in front of a DR device. The invention is based on the fact that X-ray tubes emit a wide spectrum of energies. A typical x-ray spectrum is shown in FIG. 1.

A DR detector such as flat panel detector FPD is highly efficient at all X ray energies. It is referred in this text to FPD as the detector for the digital radiography, but it should be emphasized that other digital detectors are possible without limiting the scope of the present invention. On the Other hand, the CR plate may be optimized to stop mostly low energy X rays and thus leave only the high energies to be read by the FPD detector. Therefore, the combination between the detectors can be efficiently used for dual energy techniques.

Figure 2A:
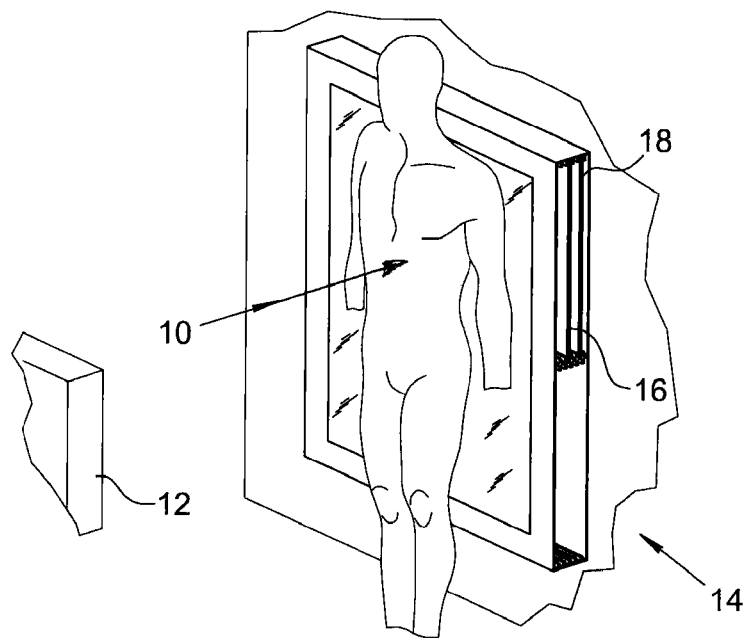
FIGS. 2a,b illustrate imaging apparatii for dual energy digital radiology in accordance with a preferred embodiment of the present invention, in two different configurations.

Reference is now made to FIG. 2a illustrating an imaging apparatus for dual energy digital radiology in accordance with a preferred embodiment of the present invention. A subject 10 is positioned between an x-ray tube 12 and set of detectors 14. The detectors preferably comprise a CR plate 16 that can be a stimulable phosphor sheet adapted to absorb radiation that was attenuated by subject 10 so as to attain information from the low energy range of the spectrum and a FPD plate 18 adapted to collect the residual photons that were not absorbed by the CR that penetrates and pass through the CR easily; those photons are likely of the high energy component of the radiation. The CR is preferably a commercial CR that is optimized for the x-ray spectrum that is shown in FIG. 1. In accordance with the method of the present invention, one exposure is being used; hence the subject is not exposed to an extensive amount of radiation and the high quality information can be attained from one exposure. Using the apparatus of the present invention, one can differentiate between high-density low-z material and lower-density high-z material. For example: in a chest image, there are nodules that are seen in the blood vessel. Few of the nodules correspond to perspective only (the vessel is oriented toward the imager) while others are calcified. Calcium is considered to be relatively a high-z material compared to the other elements in the body such as H, C and O. Using the dual energy exposure as shown in the embodiment of the present invention; it is possible to find the calcified nodules. The nodules will be seen on the bone image.

It should be noted that the CR plate is geometrically flexible; therefore, it can be added in various geometries to a fixed DR system.

The present invention provides a method for imaging a subject while utilizing dual energy through a single exposure that comprises the following steps:

The subject is being exposed to X radiation from an X ray tube in a manner that is similar to prior art exposures. Only a single exposure is performed. A stimulable phosphor sheet (CR plate) is being placed to absorb radiation that was attenuated by the subject. The plate is being optimized to absorb preferably the low energy component of the radiation. Further downstream, a position sensitive detector (DR) is placed for detecting radiation that was attenuated by the subject and the phosphor sheet while the DR detector is optimized to absorb the high energy components of the radiation.

The phosphor sheet is being scanned in order to obtain a first digital image. This image is being registered, zoomed and aligned to match exactly the DR digital image. It should be noted that the registration may include slight rotation and even non-linear stretching of the first digital image (if the CR scanner is not accurate enough).

The two images are being processed to obtain a third combined image. This combined image can be performed by normalization or any other mathematical manipulation such as subtraction techniques. In order to obtain an image having high quality and high resolution, the image can be divided into sub-areas while each sub-area is handled differently. In an extreme case, each pixel can be handles separately. Also, each sub-area can be treated in each image and only then, perform analysis together. In another case, two raw sub-areas from the two images are handles and then, a post-processing manipulation can be performed on the combined image.

Following are examples of possible manipulation of images:
1. Perform operation of linear algebra (multiply each by a constant and add/subtract). Another variant to this is to multiply each by a parameter that is in itself a function of the pixel value or a value of the pixel and its neighboring pixels.
2. Treat one image as an "indicator" image, where coordinates of a certain pixels (e.g. pixels that are easily interpreted as bones) are used to manipulate the second image, which is used as a target image, while all the other pixels are left untouched or are handled differently.
3. Choosing an ROI on one of the images and perform the analysis only in the ROI.

It should be noted that any other normalization, manipulation or handling of the images in order to obtain accurate results and high quality combined third image known in the art can be used without limiting the scope of the present invention.

There are several advantages of the method of the present invention over the available prior art as indicated herein before:
The DR image is available immediately in a digital form without the need to scan it.
High DQE.
There is no need in two exposures and the two images from two energy levels are acquired through a single exposure.
Due to the fact that the images are acquired from a single exposure, there are no motion artifacts that are mostly prone in double exposure.

Figure 2B:
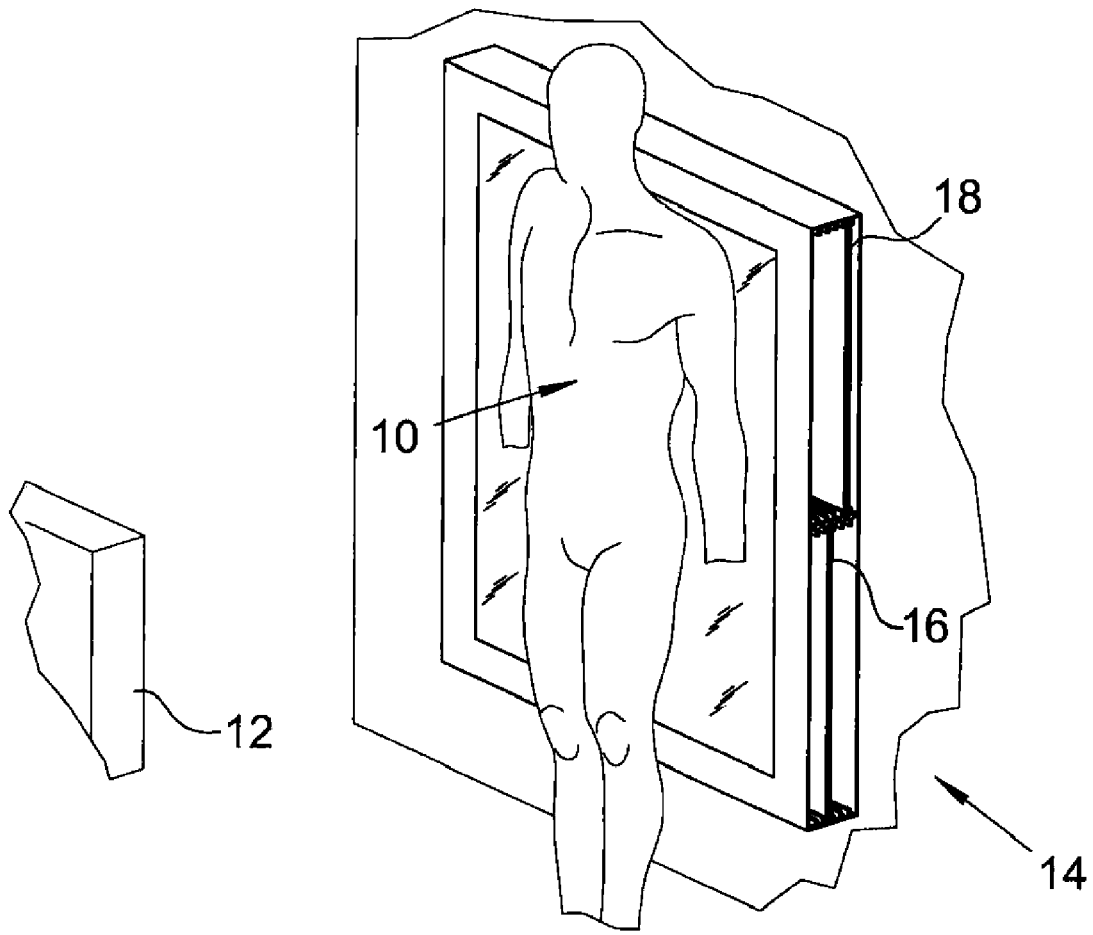

Reference is now made to FIG. 2b illustrating an imaging apparatus for dual energy digital radiology in accordance with another preferred embodiment of the present invention in a different configuration. By using this configuration, the DR plate is placed adjacent to the torso area of subject 10 while the CR plate is placed in the legs area. A single exposure is taken while acquiring an image that covers both the torso and the legs. The two images can then be stitched together. The purpose of this configuration is fitting the torso area to the DR plate and the CR to the legs area since, inherently, the CR is plate is less absorbent.

Optionally, two CR plates can be positioned adjacent different areas in the body, for example, the knee and the ankle.

Optionally, more than a single CR plate can be adjacently positioned in the system. The quantum detection efficiency (QDE) of the CR plates is relatively low, so the more energetic photons that pass through it or them are almost unattenuated. Oppositely, the DR system has high QDE and its readout and processing is instantaneous. Therefore, the DR system can be used for dose regulation (by means of automatic exposure control). The DR provides the high energy image when covered by the CR plate or plates and it images body parts of large absorption.

Figure 3:
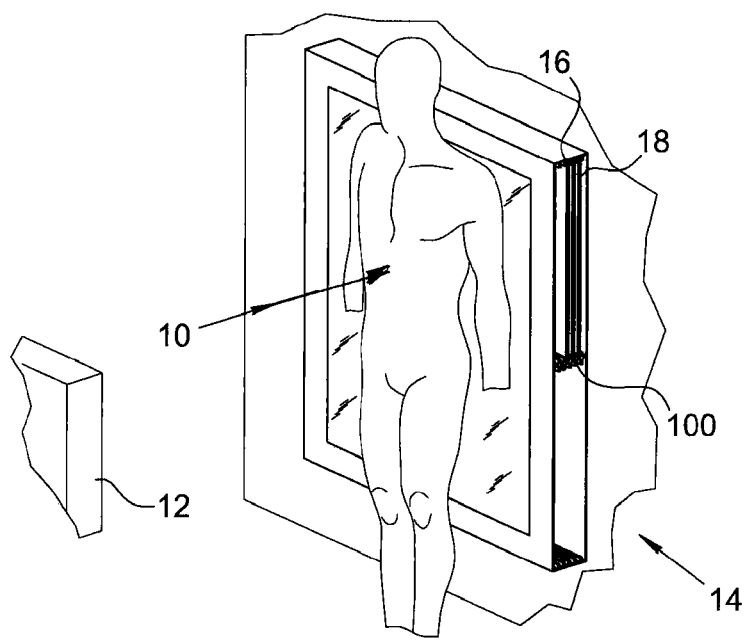
FIG. 3 illustrates an imaging apparatus for dual energy digital radiology in accordance with another preferred embodiment of the present invention.

Reference is now made to FIG. 3 illustrating an imaging apparatus for dual energy digital radiology in accordance with another preferred embodiment of the present invention. In the optional embodiment of the present invention, an additional absorbing plate 100 can be positioned between the CR and DR plates. Absorbing plate 100 is adapted to further reduce low energy radiation before the actual detection is made by the DR plate that is positioned further downstream.

Figure 4:
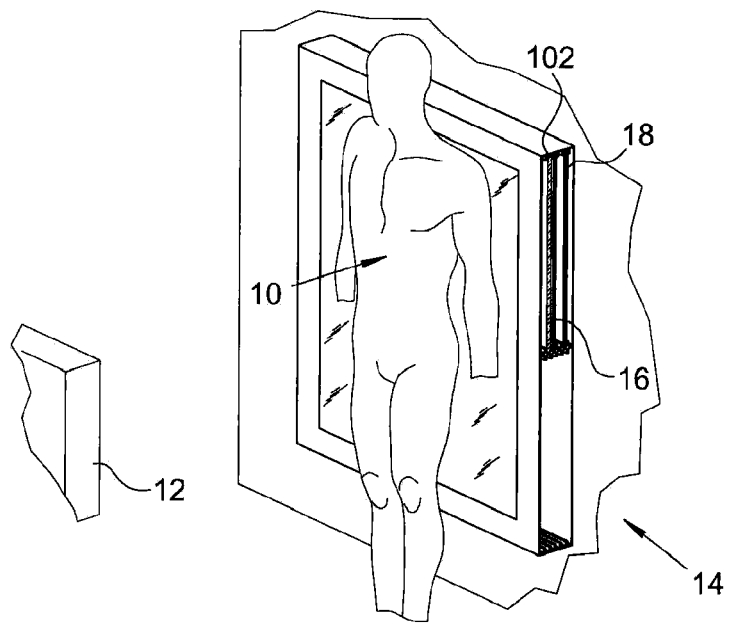
FIG. 4 illustrates an imaging apparatus for dual energy digital radiology in accordance with yet another preferred embodiment of the present invention.

Reference is now made to FIG. 4 illustrating an imaging apparatus for dual energy digital radiology in accordance with yet another preferred embodiment of the present invention. An anti-scatter grid 102 is placed between CR plate 16 and subject 10. DR system 18 is placed downstream as shown herein before.

Optionally, the anti-scatter grid can be placed between CR plate 16 and DR system 18.

Figure 5:
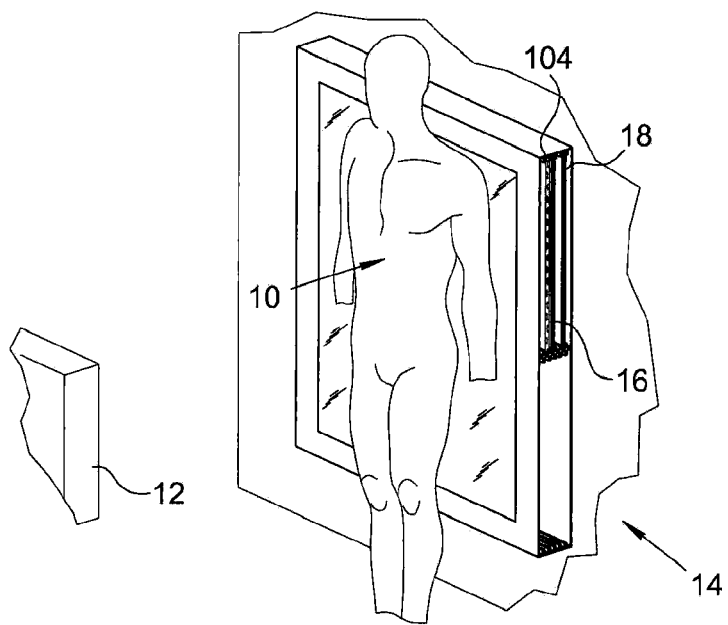
FIG. 5 illustrating an imaging apparatus for dual energy digital radiology in accordance with yet another preferred embodiment of the present invention.

Reference is now made to FIG. 5 illustrating an imaging apparatus for dual energy digital radiology in accordance with yet another preferred embodiment of the present invention. In this optional embodiment, an automatic exposure control (AEC) detector 104 is placed in front of CR plate 16, between the plate and subject 10.

Optionally the AEC detector can be placed between the CR plate and the DR.

It is optional to place the CR flexible sheet in a cassette.
It is also optional to use radio-opaque marker/s for relative alignment of the images (manually/automatic).

Automatic zooming of the CR based on calibrated distances (focal spot—CR-DR) can be performed as well in procedure of the method of the present invention.

As mentioned herein before, the DR detector of a preferred embodiment is of FPD type, however, any other detector known in the art can be used without limiting the scope of the present invention.

The DR detector is preferably a scintillator—amorphous silicon type, such as the pixium 4600 FPD made by Trixell Corp. However, any other type can be used without limiting the scope of the present invention.

It is optional to placing 2 or more CR cassettes in front of the DR detector with or without different substances between the CR cassettes for multiple energy imaging.

A plurality of configurations can be designed in order to achieve images with best quality that can be interpreted to provide structural information of the tissues. One of the applications is already described herein in which nodules can be spotted in chest images. Another application that can utilize the apparatus and method of the present invention is in the art of quantifying the calcium content in the bone, for the purpose of detecting early stages of osteoporosis. The difference between bone mineral density (BMD) scan and other DR studies is that the output of the BMD is quantitative in nature, while regular DR results are displayed in grey scale, which cannot be easily translated to chemical composition of the tissues. Using the CR-DR apparatus as shown herein for the application of BMD is similar basically to the other applications—acquiring two x-ray images of low and high energy. However, the two images are being used as two equations having two unknowns: the densities of the low z-elements (soft tissues) and the high z-elements (the bone). Calibration provides the BMD value from the high z-image.

The calibration itself can be performed using specialized phantoms. Each phantom has inserts of various size and of calcium density. The phantoms must by scanned by the CR-DR with appropriate intermediate filtration. Then, the resulting two images are combined together with algebraic parameters that are turned to give a known result for the calcium density. The obtained parameters are then used for clinical assessment of patients BMD.

It should be noted that other applications can utilize the apparatus of the present invention in order to gain other parameters needed for diagnostic purposes.

It should be clear that the description of the embodiments and attached Figures set forth in this specification serves only for a better understanding of the invention, without limiting its scope as covered by the following Claims.

It should also be clear that a person skilled in the art, after reading the present specification can make adjustments or amendments to the attached Figures and above described embodiments that would still be covered by the following Claims.

The invention claimed is:

1. An apparatus for x-ray imaging of a subject, comprising:
    an x ray source emitting a spectrum of radiation of low energy component as well as high energy component to be attenuated by the subject;
    at least one CR plate adapted to absorb mainly said radiation of low energy component that was attenuated by the subject, wherein low energy x rays image can be attained on said at least one CR plate;
    a DR plate adapted to absorb said high energy component, wherein said DR plate is placed further to said CR plate relative to the subject, so as to attain image from higher energy x rays; and
    a processor adapted to process CR and DR images obtained in a single irradiation of the subject so as to obtain a third combined processed image.

2. The apparatus as claimed in claim 1, wherein said at least one CR plate is a stimulable phosphor sheet.

3. The apparatus as claimed in claim 1, wherein said DR plate is FPD.

4. The apparatus as claimed in claim 1, wherein said at least one CR plate is configured to acquire image from a portion of the subject and wherein said DR plate is placed to acquire image from another portion of the subject.

5. The apparatus as claimed in claim 1, wherein an absorbing plate is further placed adjacent to said at least one CR plate or said DR plate.

6. The apparatus as claimed in claim 5, wherein said absorbing plate is placed between said at least one CR plate and said DR plate.

7. The apparatus as claimed in claim 1, wherein an anti-scatter grid is farther placed adjacent to said at least one CR plate or said DR plate.

8. The apparatus as claimed in claim 7, wherein said anti-scatter grid is placed between said at least one CR plate and said DR plate.

9. The apparatus as claimed in claim 1, wherein an ABC detector is placed between said at least one CR plate and said DR plate.

10. The apparatus as claimed in claim 1, wherein an ABC detector is placed between said at least one CR plate and the subject.

11. The apparatus as claimed in claim 1, wherein said DR plate is placed within a bucky that is provided with rails adapted to receive at least one of said at least one CR plate.

12. The apparatus as claimed in claim 1, wherein said DR plate is a scintillator-amorphous silicon type.

13. A method of x-ray imaging of a subject comprising:
    exposing the subject to X radiation;
    placing at least one CR plate adapted to absorb said radiation that was attenuated by the subject, said at least one CR plate is optimized to absorb preferably a low energy component of said radiation;
    placing further downstream a DR detector for detecting radiation that was attenuated by the subject and said at least one CR plate, wherein said detector is optimized to absorb the high energy components of the radiation;
    scanning said at least one CR plate to obtain a first digital image;
    processing said first digital image to match exactly DR image; and
    obtaining a third combined image by processing said first digital image and said DR image.

14. The method as claimed in claim 13, wherein said processing said first digital image comprises registering, zooming, and aligning.

15. The method as claimed in claim 13, further comprising placing an absorbing plate adjacent said at least one CR plate.

16. The method as claimed in claim 13, further comprising placing an anti-scatter grid adjacent said at least one CR plate.

17. The method as claimed in claim 13, further comprising placing an AEC detector adjacent said at least one CR plate.

18. The method as claimed in claim 13, wherein obtaining a third combined image is performed by linear algebra operations such as multiply each by a constant, add/subtract, or multiply each by a parameter that is in itself a function of the pixel value or a value of the pixel and its neighboring pixels.

19. The method as claimed in claim 13, wherein obtaining a third combined image is performed by treating said first digital image as an "indicator" image, where coordinates of certain pixels are used to manipulate the DR image, which is used as a target image, while all the other pixels are left untouched or are handled differently.

20. The method as claimed in claim 13, wherein obtaining a third combined image is performed by choosing an ROI on one of said first digital image or said DR image and perform an analysis only in said ROI.

21. The method as claimed in claim 13, wherein said method further comprising calculating BMD values said first digital image and said DR image.

22. The method as claimed in claim 13, wherein said method further comprises finding calcified nodules in bone imaged on said third combined image.

* * * * *